US00PP22553P2

(12) United States Plant Patent
Pieters

(10) Patent No.: US PP22,553 P2
(45) Date of Patent: Mar. 6, 2012

(54) ***CHRYSANTHEMUM* PLANT NAMED 'YELLOW GREENRUNNER'**

(50) Latin Name: *Chrysanthemum×morifolium*
Varietal Denomination: Yellow Greenrunner

(75) Inventor: Luc Remi Johan Pieters, Staden-Oostnieuwkerke (BE)

(73) Assignee: Pieters Joseph & Luc B.V.B.A, Staden-Oostnieuwkerke (BE)

( * ) Notice: Subject to any disclaimer, the term of this patent is extended or adjusted under 35 U.S.C. 154(b) by 0 days.

(21) Appl. No.: 13/066,467

(22) Filed: Apr. 14, 2011

(51) Int. Cl.
*A01H 5/00* (2006.01)

(52) U.S. Cl. ..... Plt./289

(58) Field of Classification Search ..... Plt./289
See application file for complete search history.

(56) References Cited

U.S. PATENT DOCUMENTS

PP14,414 P3 * 12/2003 Pieters ..... Plt./289
PP16,935 P2 * 8/2006 Utecht ..... Plt./325

OTHER PUBLICATIONS

UPOV ROM GTITM Computer Database, GTI Jouve Retrieval Software 2011/01 Citation for 'Yellow Greenrunner'.*

* cited by examiner

*Primary Examiner* — Wendy C Haas
(74) *Attorney, Agent, or Firm* — C. A. Whealy

(57) ABSTRACT

A new and distinct cultivar of *Chrysanthemum* plant named 'Yellow Greenrunner', characterized by its uniform, upright, outwardly spreading and rounded plant habit; moderately vigorous growth habit; freely branching habit; dense and full plant habit; freely flowering habit; decorative-type inflorescences with yellow-colored ray florets; long flowering period; and excellent garden performance.

2 Drawing Sheets

Botanical designation: *Chrysanthemum×morifolium.*
Cultivar denomination: 'YELLOW GREENRUNNER'.

BACKGROUND OF THE INVENTION

The present invention relates to a new and distinct cultivar of *Chrysanthemum* plant, botanically known as *Chrysanthemum×morifolium* and hereinafter referred to by the name 'Yellow Greenrunner'.

The new *Chrysanthemum* plant is a naturally-occurring whole plant mutation of *Chrysanthemum×morifolium* 'Green Runner', not patented. The new *Chrysanthemum* plant was discovered and selected by the Inventor as a flowering plant from within a population of plants of 'Green Runner' in a controlled greenhouse environment in Staden-Oostnieuwkerke, Belgium in October, 2007.

Asexual reproduction of the new *Chrysanthemum* plant by vegetative cuttings was first conducted in a controlled greenhouse environment in Staden-Oostnieuwkerke, Belgium in February, 2008. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environment such as temperature, daylength and light intensity, without, however, any variance in genotype.

The following traits have been repeatedly observed and are determined to be the unique characteristics of 'Yellow Greenrunner'. These characteristics in combination distinguish 'Yellow Greenrunner' as a new and distinct *Chrysanthemum* plant:

1. Uniform, upright, outwardly spreading and rounded plant habit; moderately vigorous growth habit.
2. Freely branching habit; dense and full plant habit.
3. Freely flowering habit.
4. Decorative-type inflorescences with yellow-colored ray florets.
5. Long flowering period.
6. Excellent garden performance.

Plants of the new *Chrysanthemum* differ primarily from the mutation parent, 'Green Runner', in ray floret color as plants of 'Green Runner' have white-colored ray florets.

Plants of the new *Chrysanthemum* can also be compared to plants of *Chrysanthemum×morifolium* 'Tardel', not patented. In side-by-side comparisons conducted in Staden-Oostnieuwkerke, Belgium, plants of the new *Chrysanthemum* differed from plants of 'Tardel' in the following characteristics:

1. Plants of the new *Chrysanthemum* flowered earlier than plants of 'Tardel'.
2. Plants of the new *Chrysanthemum* had decorative type inflorescences whereas plants of 'Tardel' had daisy type inflorescences.
3. Plants of the new *Chrysanthemum* and 'Tardel' differed in ray floret color as plants of 'Tardel' had darker yellow-colored ray florets.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering plant of 'Yellow Greenrunner' grown in a container.

The photograph on the second sheet are close-up views of the upper and lower surfaces of typical inflorescences (left) of 'Yellow Greenrunner' and upper and lower surfaces of typical leaves (right) of 'Yellow Greenrunner'.

DETAILED BOTANICAL DESCRIPTION

The aforementioned photographs and following observations and measurements describe plants grown during the summer and autumn in 19-cm containers in an outdoor nursery in Staden-Oostnieuwkerke, Belgium and under conditions and practices which approximate those generally used in commercial *Chrysanthemum* production. During the production of the plants, day temperatures ranged from 10° C. to 25° C. and night temperatures ranged from 5° C. to 15° C. Plants were 5.5 months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Yellow Greenrunner'.

Parentage: Naturally-occurring whole plant mutation of *Chrysanthemum×morifolium* 'Green Runner', not patented.

Propagation:

*Type.*—Terminal vegetative cuttings.

*Time to initiate roots, summer.*—About 14 days at temperatures of about 20° C.

*Time to initiate roots, winter.*—About 20 days at temperatures of about 20° C.

*Time to produce a rooted young plant, summer.*—About 30 days at temperatures of about 20° C.

*Time to produce a rooted young plant, winter.*—About 40 days at temperatures of about 20° C.

*Root description.*—Fine, fibrous; light brown in color.

*Rooting habit.*—Freely branching; medium density.

Plant description:

*Appearance.*—Perennial *Chrysanthemum* with decorative type inflorescences; stems upright and outwardly spreading giving a uniformly rounded appearance to the plant; very freely branching habit with about 25 lateral branches developing per plant; pinching enhances lateral branch development; dense and full plant habit; moderately vigorous growth habit.

*Plant height.*—About 36.5 cm.

*Plant width.*—About 61 cm.

*Lateral branches.*—Length: About 31 cm. Diameter: About 4 mm. Internode length: About 1.7 cm. Strength: Strong. Aspect: Lateral branches positioned about 30° from the main stem. Texture: Densely pubescent; longitudinally ridged. Color: Close to 145A to 145B.

*Leaves.*—Arrangement: Alternate, simple. Length: About 3.4 cm. Width: About 2.7 cm. Shape: Roughly ovate, three-lobed. Apex: Acute. Base: Attenuate. Margin: Palmately lobed and coarsely dentate, sinuses between lateral lobes divergent to parallel. Texture, upper and lower surfaces: Densely pubescent. Venation pattern: Pinnate. Color: Developing leaves, upper surface: Close to 143A. Developing leaves, lower surface: Close to 147B. Fully expanded leaves, upper surface: Close to 137C and 138A; venation, close to 138A to 138B. Fully expanded leaves, lower surface: Close to 147B; venation, close to 147B. Petiole: Length: About 1 cm. Diameter: About 2 mm. Texture, upper and lower surfaces: Densely pubescent. Color, upper surface: Close to 144A to 144B. Color, lower surface: Close to 146C to 146D.

Inflorescence description:

*Appearance.*—Decorative inflorescence form; inflorescences borne on terminals above foliar plane; disc and ray florets arranged acropetally on a capitulum.

*Fragrance.*—Moderately fragrant, pungent.

*Flowering response.*—Long flowering period; under natural season conditions, plants flower continuously from mid-September to late October in Belgium.

*Postproduction longevity.*—Inflorescences maintain good color and substance for about three weeks in an outdoor nursery; inflorescences not persistent.

*Quantity of inflorescences.*—About 50 inflorescences develop per lateral branch; about 1,250 inflorescences per plant.

*Inflorescence bud.*—Height: About 6 mm. Diameter: About 6 mm. Shape: Globular. Color: Close to 146B.

*Inflorescence size.*—Diameter: About 2.9 cm. Depth (height): About 1.4 cm. Receptacle diameter: About 3 mm. Receptacle height: About 3 mm. Receptacle color: Close to 145C.

*Ray florets.*—Length: About 1.3 cm. Width: About 5 mm. Shape: Narrowly obovate. Apex: Emarginate. Base: Cuneate. Margin: Entire. Aspect: About 65° from vertical. Texture, upper and lower surfaces: Smooth, glabrous; longitudinally ridged. Number of ray florets per inflorescence: About 150. Color: When opening, upper surface: Close to 6A to 6B. When opening, lower surface: Close to 7C to 7D. Fully opened, upper surface: Close to 7C to 7D; color does not change with development. Fully opened, lower surface: Close to 8B to 8C; color does not change with development.

*Disc florets.*—No disc florets observed.

*Phyllaries.*—Number of phyllaries per inflorescence: About 24 arranged in about three whorls. Length: About 6 mm. Width: About 2.5 mm. Shape: Ovate. Apex: Bluntly acute. Base: Cuneate. Margin: Entire. Texture, upper surface: Smooth, glabrous. Texture, lower surface: Pubescent. Color, upper and lower surfaces: Close to 147B; margins, close to 200B.

*Peduncles.*—Length, terminal peduncle: About 4.6 cm. Length, fourth peduncle: About 4.5 cm. Diameter: About 1.5 mm. Aspect: Erect to about 30° from vertical. Strength: Strong. Texture: Densely pubescent. Color: Close to 138C.

*Reproductive organs.*—Androecium: Not observed. Gynoecium: Not observed.

*Seed/fruit.*—Seed and fruit production have not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance, are hardy to USDA Hardiness Zones 7 to 8 and will tolerate high temperatures of about 35° C.

It is claimed:

1. A new and distinct *Chrysanthemum* plant named 'Yellow Greenrunner' as illustrated and described.

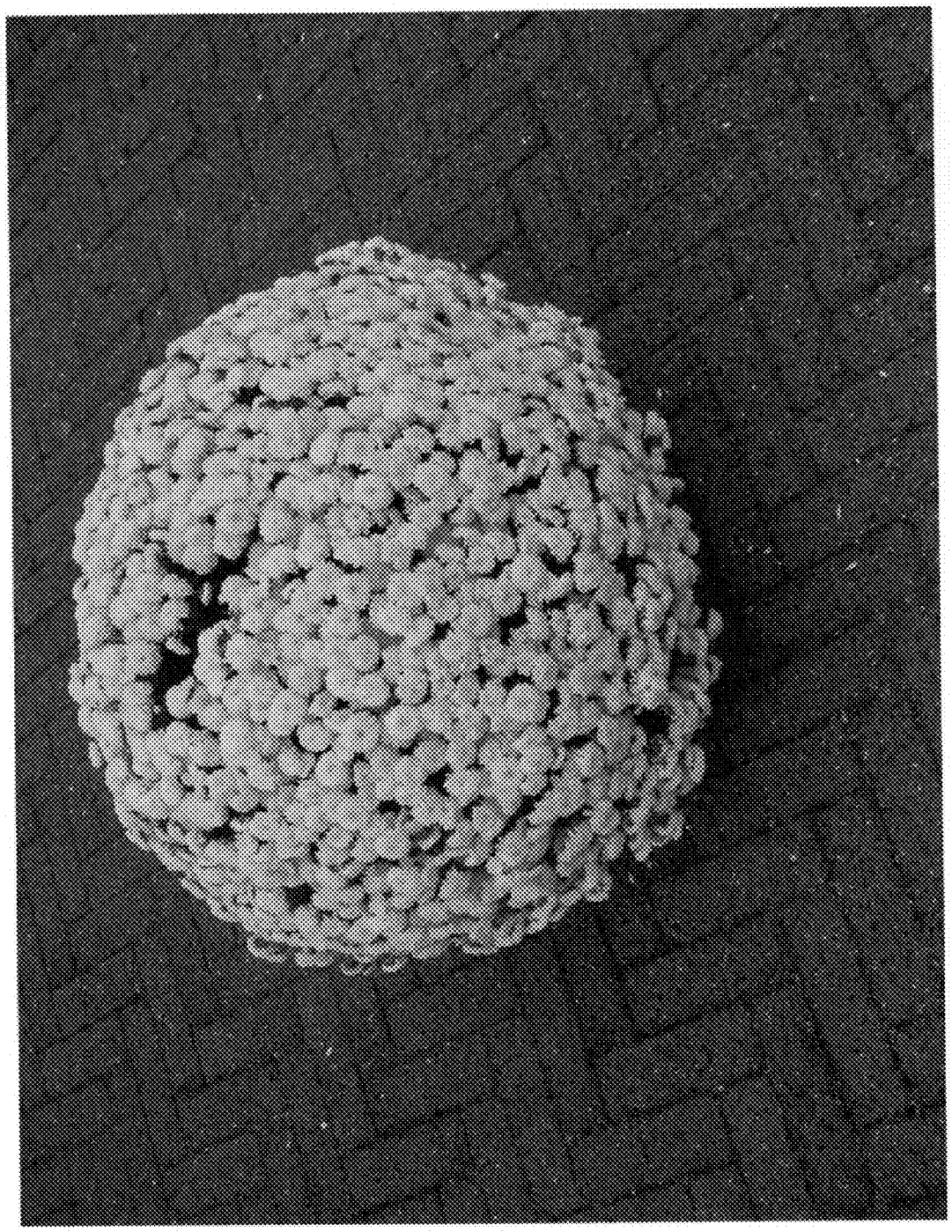

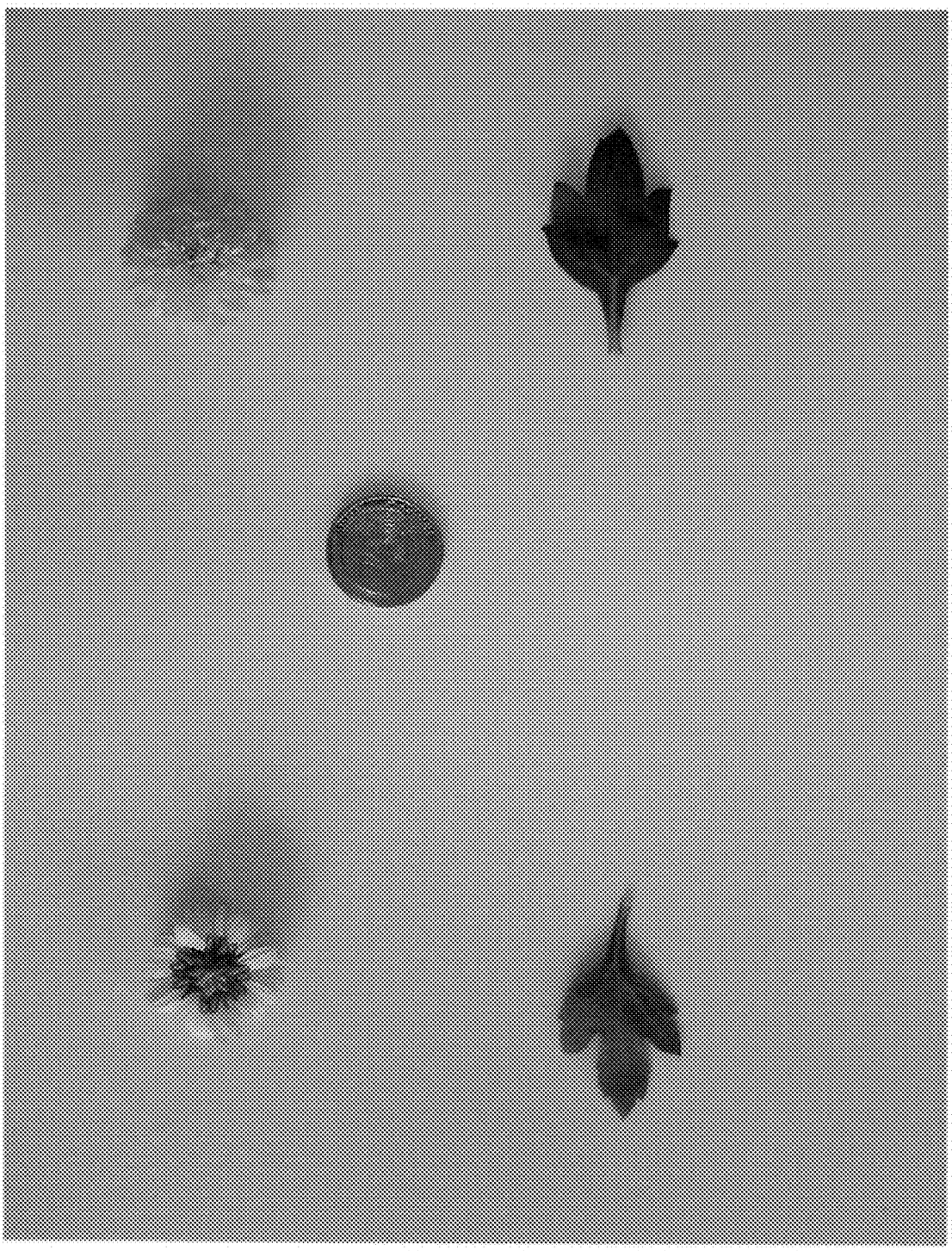

* * * * *